United States Patent
Mielenz

(10) Patent No.: US 9,638,615 B2
(45) Date of Patent: May 2, 2017

(54) METHOD AND CONTROL DEVICE AND DETECTION DEVICE FOR RECOGNIZING AN ENTRY OF A MOTOR VEHICLE INTO A TRAFFIC LANE OPPOSITE A DRIVING DIRECTION

(71) Applicant: Robert Bosch GmbH, Stuttgart (DE)

(72) Inventor: Holger Mielenz, Ostfildern (DE)

(73) Assignee: ROBERT BOSCH GMBH, Stuttgart (DE)

( * ) Notice: Subject to any disclaimer, the term of this patent is extended or adjusted under 35 U.S.C. 154(b) by 112 days.

(21) Appl. No.: 14/553,570

(22) Filed: Nov. 25, 2014

(65) Prior Publication Data
US 2015/0145699 A1    May 28, 2015

(30) Foreign Application Priority Data
Nov. 26, 2013 (DE) .................. 10 2013 224 171

(51) Int. Cl.
| | | |
|---|---|---|
| G08G 1/01 | (2006.01) | |
| G01N 5/02 | (2006.01) | |
| F02M 25/08 | (2006.01) | |
| G01H 13/00 | (2006.01) | |
| G08G 1/056 | (2006.01) | |

(52) U.S. Cl.
CPC ............. *G01N 5/02* (2013.01); *F02M 25/089* (2013.01); *G01H 13/00* (2013.01); *G08G 1/056* (2013.01)

(58) Field of Classification Search
CPC ..................................... G01G 1/056
USPC ............................................. 340/935
See application file for complete search history.

(56) References Cited

U.S. PATENT DOCUMENTS

| | | | |
|---|---|---|---|
| 5,777,564 A * | 7/1998 | Jones ................. | G08G 1/08 340/907 |
| 8,258,935 B2 * | 9/2012 | Hashimoto ........... | B60W 50/14 180/167 |
| 8,428,861 B1 * | 4/2013 | Williams .............. | G08G 1/164 701/301 |
| 9,123,242 B2 * | 9/2015 | Takahashi ............ | G06K 9/72 |
| 2004/0193347 A1 * | 9/2004 | Harumoto ............ | B60T 8/1755 701/45 |
| 2009/0102683 A1 * | 4/2009 | May ..................... | E01F 9/696 340/907 |
| 2011/0121992 A1 * | 5/2011 | Konaka ................ | B62D 15/029 340/905 |
| 2013/0044009 A1 * | 2/2013 | Tagawa ................ | G08G 1/075 340/995.28 |
| 2013/0147639 A1 * | 6/2013 | Wietfeld .............. | G08G 1/056 340/905 |
| 2013/0338850 A1 * | 12/2013 | Takahara ............. | G01C 21/3697 701/1 |
| 2014/0232566 A1 * | 8/2014 | Mimeault ............. | G01S 17/023 340/935 |

* cited by examiner

*Primary Examiner* — Eric M Blount
(74) *Attorney, Agent, or Firm* — Gerard Messina

(57) ABSTRACT

In a method for recognizing an entry of a motor vehicle into a traffic lane of a road opposite a driving direction of the traffic lane, a stop line of the traffic lane is detected and a wrong driving direction of the motor vehicle is recognized if the motor vehicle has crossed the stop line upon entry into the traffic lane.

10 Claims, 3 Drawing Sheets

METHOD AND CONTROL DEVICE AND DETECTION DEVICE FOR RECOGNIZING AN ENTRY OF A MOTOR VEHICLE INTO A TRAFFIC LANE OPPOSITE A DRIVING DIRECTION

BACKGROUND OF THE INVENTION

1. Field of the Invention

The present invention relates to a method and a control device and detection device for recognizing an entry of a motor vehicle into a traffic lane of a road opposite a driving direction of the traffic lane.

2. Description of the Invention

In the event of an accident, wrong-way drivers, also referred to as ghost drivers, cause deaths, injuries and significant material damage. Wrong-way driving is understood here to mean driving in a traffic lane or a roadway opposite the prescribed driving direction.

The recognition of wrong-way driving with the aid of navigation devices is not always reliably possible, since the information of the navigation device, such as road category and road direction, is provided too late for most cases of wrong-way driving, i.e., the vehicles at that point are already traveling opposite the driving direction.

Modern motor vehicles use inertial sensors, such as acceleration sensors and yaw rate sensors, as well as the steering angle for determining the state of the vehicle, in order to implement safety systems and comfort systems. In addition, a variety of modern motor vehicles today have an internal GPS module, for example, for a navigation system or for determining the position of the motor vehicle. Presently and in the future, more and more motor vehicles will be equipped with video sensors, which also process and output various information.

BRIEF SUMMARY OF THE INVENTION

The method according to the present invention for detecting an entry of a motor vehicle into a traffic lane of a road opposite the driving direction of the traffic lane includes, in principle, the following steps:

detection of a stop line of the traffic lane;
  recognition of a wrong driving direction of the motor vehicle, if the motor vehicle has crossed the stop line upon entering the traffic lane.

The method according to the present invention has the advantage that the driver of the motor vehicle is quickly and reliably informed that he is moving opposite the free or prescribed driving direction in a road or in a traffic lane, or that he is running the risk of turning into or driving into a road opposite the driving direction. This situation may arise during the process of turning at an intersection or, for example, when entering a highway entrance. The method may be based purely on the available sensors of the vehicle and may therefore be quickly implemented. The simple detection and recognition of a stop or stop line makes the method simple and reliable.

According to a preferred specific embodiment of the present invention, it is provided that a street light signal system is detected, the light signal system is associated with a traffic lane and a wrong driving direction is recognized when the stop line is farther away from the motor vehicle than the traffic light. This additional criterion increases the reliability of the method and may detect or check for plausibility of potential wrong-way driving even before a stop line is crossed.

It is also possible that a street light signal system is detected, the light signal system is associated with a traffic lane and a wrong driving direction is recognized when a reverse side of the light signal system is detected. This additional criterion may further increase the reliability and may also recognize or check for plausibility of potential wrong-way driving before a stop line is crossed.

It is further possible that a wrong driving direction is recognized when a navigation system of the motor vehicle detects a position of the motor vehicle in the traffic lane. This is also an additional criterion for checking for plausibility or determining wrong-way driving. On the basis of navigation data and/or a determination of the position of the vehicle, such as a global positioning system (GPS), it is possible to ascertain the position or a movement direction or trajectory of the vehicle and to compare it with map material.

In one particular specific embodiment, it is provided that as the motor vehicle enters a traffic lane, kinematic data of the motor vehicle are compared in order to detect a wrong driving direction. Thus, it may be detected early or in advance of the entry whether the motor vehicle is moving on a correct trajectory. For this purpose, kinematic data may be used, which are obtained from the sensors of the vehicle such as, for example, the speed, the steering angle, the steering angle speed and/or the steering angle path. The use of additional variables, which may also be derived or considered in combination, is equally possible. Based on the variables ascertained during driving, it is possible using a simple comparison or using a classification method to detect or to predict whether the vehicle is moving on a correct or improper trajectory, i.e., on one which is leading to driving the wrong way.

It is further possible that the kinematic data of the motor vehicle are compared with the kinematic data of a database. This allows for a rapid and reliable comparison. The database may contain geo-referenced kinematic data.

The motor vehicle may transmit the kinematic data of the motor vehicle to a database. Thus, the data are at least not exclusively prepared with the aid of analytical methods, but rather are transmitted instantaneously based on the actual driving situations to a server or a central location. This transmission may be implemented, for example, by a smartphone or a communications link of the motor vehicle. The data may then be provided to all users or vehicles. By aggregating, if necessary, large amounts of data, it may be ascertained which driving behavior is possible for the instantaneous traffic situation. Thus, for example, speeds and accelerations for a particular location may be stored. The instantaneous and/or the next expected maneuver of a driver may then be classified by predicting the trajectories on the basis of the location-related speed, longitudinal acceleration and lateral acceleration.

It is advantageously provided that a driver of the motor vehicle may be informed acoustically, haptically and/or visually upon recognition of a wrong driving direction. Thus, wrong-way driving may be avoided or at least corrected immediately after wrong-way driving has begun. Interventions in the operation of the motor vehicle are also conceivable, for example, a braking, in order to inform the driver of the instantaneous situation.

According to the present invention, a control device and detection device are provided for recognizing an entry of a motor vehicle into a traffic lane of a road opposite the driving direction of the traffic lane, including means for detecting a stop line of the traffic lane and means for recognizing a wrong driving direction of the motor vehicle when the motor vehicle has crossed the stop line upon entering the traffic lane. The same advantages and modifications as described above apply.

The means for detecting may include at least a visual ambient sensor, preferably a video camera. The means for recognizing may include a controller or control device or a suitable processing unit.

The aforementioned criteria for recognizing or checking for plausibility, i.e., surmising or assessing wrong-way driving, may be considered or applied individually or collectively. When considered individually, wrong-way driving is detected given one single criterion. When considered collectively, wrong-way driving is recognized and checked for plausibility when multiple criteria are met. The aforementioned criteria are: if the motor vehicle has crossed the stop line upon entering the traffic lane, if the stop line is farther away from the motor vehicle than the traffic light, if a rear side of the light signal system is detected, if a navigation system of the motor vehicle detects a position of the motor vehicle in the traffic lane, if kinematic data of the motor vehicle are compared as the motor vehicle enters a traffic lane.

DETAILED DESCRIPTION OF THE INVENTION

Figure 1:
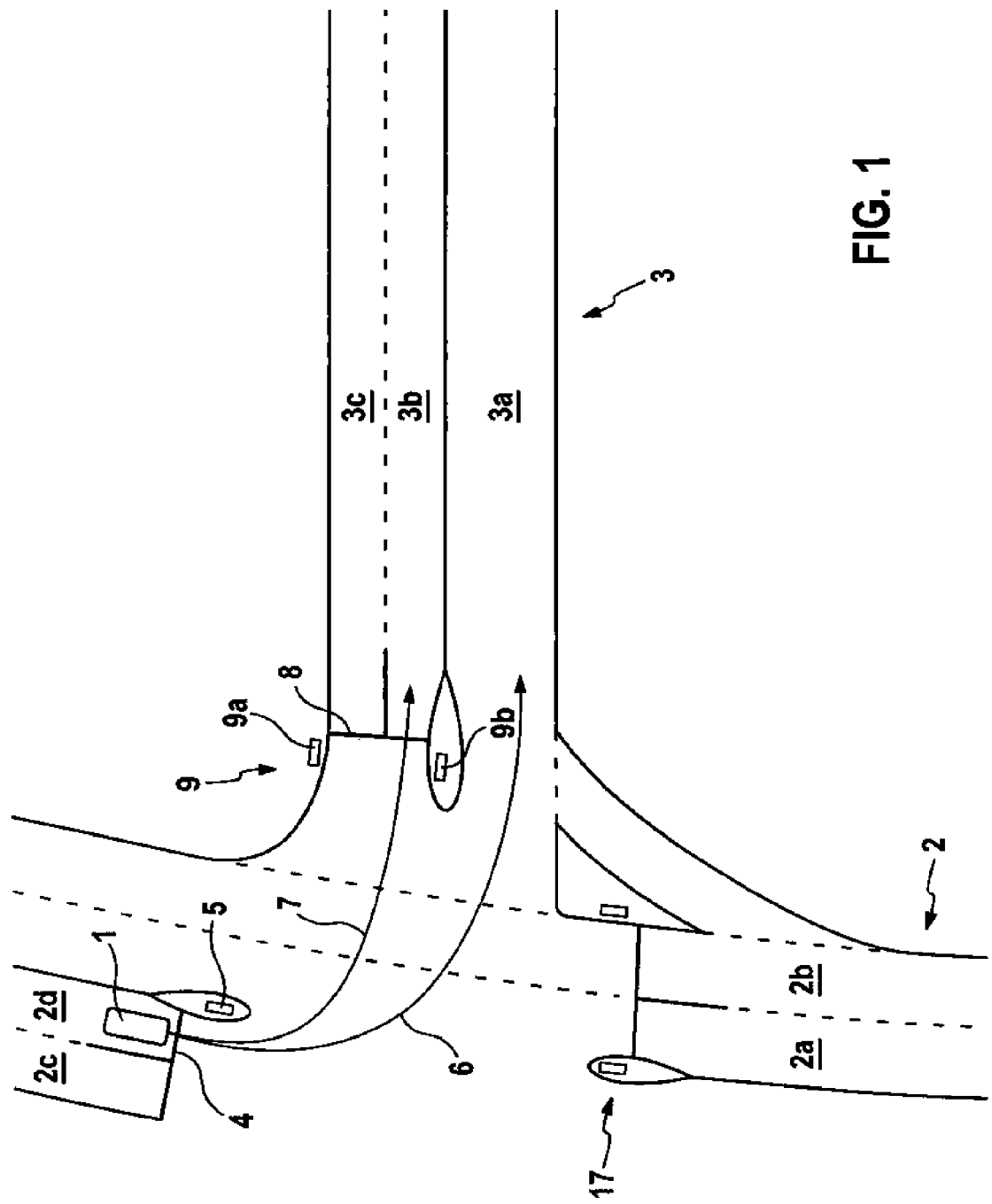
FIG. 1 schematically shows a representation of an entry of a motor vehicle into a traffic lane.

FIG. 1 shows a motor vehicle 1, which is driving on a first road 2 and is about to turn into or enter a second road 3. In the case depicted in FIG. 1, the two roads 2 and 3 form an intersection.

Road 2 has multiple traffic lanes or motorways 2a, 2b, 2c and 2d. The two traffic lanes 2a and 2b form a roadway; this may also be a divided directional roadway, which in this case, for example, includes a driving direction from bottom to top. The two traffic lanes 2c and 2d have an oppositely prescribed driving direction.

Motor vehicle 1 is driving in the proper driving direction, or is stopped in front of a stop line 4 in case a light signal system 5 is not allowing the vehicle to proceed further.

The term vehicle or motor vehicle is understood here to mean all powered modes of transportation such as, for example, passenger vehicles, trucks, busses, motorcycles, etc.

Second road 3 also includes multiple traffic lanes 3a, 3b and 3c. For vehicle 1, which is turning or entering, traffic lane 3a shows the proper driving direction. In this case, traffic lane 3a is the only traffic lane having the correct driving direction. Road 3 may, of course, also include multiple traffic lanes with this driving direction. Traffic lane 3a could, for example, be entered on a trajectory or line of movement 6. The two traffic lanes 3b and 3c include a prescribed driving direction opposite that of traffic lane 3a. Turning into one of these two traffic lanes 3b or 3c on trajectory 7 would result in motor vehicle 1 driving the wrong way.

The two traffic lanes 3b and 3c of second road 3 are delimited in the area of intersection by a solid, usually white stop line 8. Traffic lane 3a has no such line or delimitation.

Associated with the two traffic lanes 3b and 3c in the area of the intersection is a light signal system or traffic light 9. Instead of two traffic lanes 3b and 3c in this driving direction, road 3 may also have just one traffic lane. Light signal system 9 includes two signalers 9a and 9b, signaler 9a being situated at the right margin of the lane of road 3 and signaler 9b being situated on a traffic island to the left of traffic lane 3b. The two signalers 9a and 9b may be synchronously connected, i.e., they apply to the two traffic lanes 3b and 3c, or they may display signals specific to the two traffic lanes 3b and 3c.

From the perspective of a motor vehicle, which is moving in one of traffic lanes 3b or 3c, the two signalers 9a and 9b are discernible from their front side, and are situated—as seen from the vehicle—behind stop line 8. From the perspective of a vehicle potentially or presently driving the wrong way along trajectory 7, the rear sides of signalers 9a and 9b are discernible, which are then situated in front of stop line 8. Instead of two signalers 9a, 9b, an individual signaler may also be provided.

It will be explained later how the directional information of road 3 or of individual traffic lanes 3a, 3b and 3c may be used in order to check for plausibility or to detect a wrong-way driving of motor vehicle 1. The direction-related features described are stop line 8, front sides or rear sides of signalers 9a and 9b as well as the position of signalers 9a, 9b in relation to stop line 8.

Figure 2:
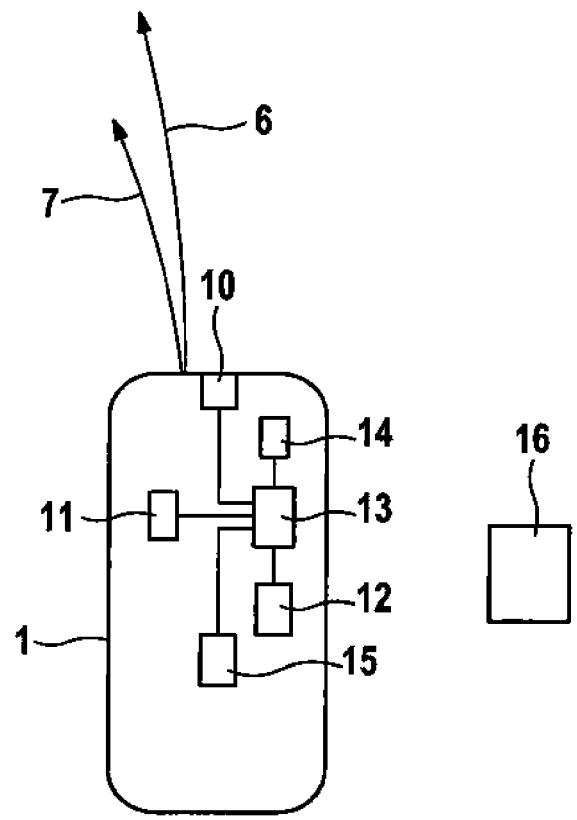
FIG. 2 schematically shows a motor vehicle including a control device and a detection device.

FIG. 2 schematically depicts motor vehicle 1. Motor vehicle 1 includes a control unit and detection unit for recognizing an entry of motor vehicle 1 into a traffic lane 3b of a road 3 opposite a driving direction of traffic lane 3b.

Motor vehicle 1, respectively, the control device and detection device, includes a visual ambient sensor 10, for example, a video camera. In addition, motor vehicle 1, respectively, the control device and detection device, includes at least one additional sensor 11, which in this case may be presented as exemplary of a number of sensors. Sensor 11 may include, for example, an acceleration sensor, a radar sensor, a steering angle sensor or the like, in order to detect kinematic data of motor vehicle 1. Also provided is a navigation module or navigation device 12, which may include a GPS functionality and navigation data such as map material. A controller 13 is connected to visual ambient sensor 10, to additional sensor or sensors 11 and to navigation system 12. This may be a wired or wireless connection. Controller 13 is also connected to a memory 14, which is used, for example, to store data, such as comparison values or verification values for the directional information, or for storing kinematic data. Controller 13 is further connected to a communication interface 15, which is configured to communicate with an external unit 16, such as a central server.

Sensors 10 and 11, navigation device 12, controller 13, memory 14 and communication interface 15 may—as depicted here—be designed as independent units, or they may be integrated in one or multiple units. In particular, each component is not required to be implemented in hardware; individual functions may also be implemented as software routines or programs.

With the aid of communication interface 15, it is possible to provide motor vehicle 1, respectively, the control device and detection device, with information, such as map data or kinematic data, and/or functionalities, such as access to programs of external device 16.

Described below with reference to FIG. 3, viewed together with FIG. 1, is a method for recognizing an entry of a motor vehicle into a traffic lane of a road opposite a driving direction of the traffic lane.

In general, the method ascertains the driving direction of traffic routes ahead, and predicts or detects the driving behavior of the driver or of motor vehicle 1, in order to recognize a turning or entry opposite the driving direction provided.

In a first step 100, an entry or a turning of motor vehicle 1, in the example here, from first road 2 into second road 3, is detected or predicted. This may be based on signals of sensors 10 and/or 11, or of navigation system 12 or on inputs by the driver such as, for example, the setting of the direction indicator.

In a further step 110, stop line 8 of the two traffic lanes 3b and 3c is detected by visual ambient sensor 10.

Subsequently, i.e., when motor vehicle 1 moves along trajectory 7, the crossing of stop line 8 by motor vehicle 1 may be detected. No stop line is crossed, however, if motor vehicle 1 moves on correct trajectory 6. Wrong-way driving may be detected in a step 190 based on the crossing or non-crossing of stop line 8.

Parallel thereto or alternatively, light signal system 9, or signalers 9a and 9b, are detected by visual ambient sensor 10 in a step 130.

In another step 140, an algorithm based on image processing, for example, associates a traffic lane with the light signal system, in this case, for example, signaler 9b with traffic lane 3b. This algorithm may, as may be the entire method, be carried out in controller 13, in central unit 16 or distributed among various systems. The light signal system may be associated, for example, due to its proximity next to or above a recognized roadway or a recognized traffic lane.

In a step 110, a stop line 8 of traffic lane 3b, 3c is again detected. Subsequently, in step 150, the geometric relation between light signal system 9 and stop line 8 is determined. More precisely, it is determined whether, from the perspective of motor vehicle 1, light signal system 9 is situated in front of or behind stop line 8. Or it is determined whether stop line 8 or light signal system 9 is farther away from the vehicle than light signal system 9 or stop line 8.

In step 190, wrong-way driving may then be detected, if motor vehicle 1 is moving on trajectory 7, since there stop line 8—as seen from motor vehicle 1—is situated behind light signal system 9. This criterion is not met when travelling on trajectory 6, so that a correct travel is given. The relevant stop lines are considered to be those which are closest to the light signal system.

In addition, light signal system 9 is again detected by ambient sensor 10 parallel thereto or alternatively in a step 130.

If in a step 160 signaler 9a and/or 9b is/are then classified, for example, with reference to its/their geometric shape, however, no light signal being ascertained, then it is certain that the motor vehicle discerns the rear side of light signal system 9. Thus, in step 190, wrong-way driving may be detected. In turn, light signal system 9 may be associated with a traffic lane 3b and/or 3c in a step 140.

The above described three detection and classification paths evaluate all directional features of road 3 recorded via visual ambient sensor 10. Visual ambient sensor 10 may be situated, designed or evaluated in such a way that only information, which is found in a certain spatial proximity to trajectories 6 or 7, may be detected or taken into account. For example, it may be provided that when driving on trajectory 6 or 7, light signal 9 is taken into account, whereas a light signal system 17 for the two traffic lanes 2a and 2b is not taken into account. Such driving situation-related filtering of information reduces the flow of data and simultaneously increases the reliability of the method. If, however, motor vehicle 1 moves along another trajectory, in order, for example, to enter traffic lanes 2a and 2b, light signal system 17 with its associated stop line is considered to be relevant, while light signal system 9 with associated stop line 8 is then classified as irrelevant or is not detected.

In another path, kinematic data of motor vehicle 1 are detected in parallel or alternatively with sensors 11. These kinematic data include, for example, speed, acceleration, steering angle, steering angle path, as well as steering angle speed. These data are then transmitted with the aid of communication interface 15 to external device 16, where they are stored and processed in a database, for example. There, the data are stored geo-referenced, i.e., assigned a location.

In another step 180, the ascertained kinematic data of motor vehicle 1 are compared with kinematic data from the database, so that it may be determined whether motor vehicle 1 is moving on correct trajectory 6 or on a trajectory 7, which leads to driving the wrong way.

In step 190, wrong-way driving may be detected if the kinematic data of motor vehicle 1 coincide with the stored kinematic data of trajectory 7.

Figure 3:
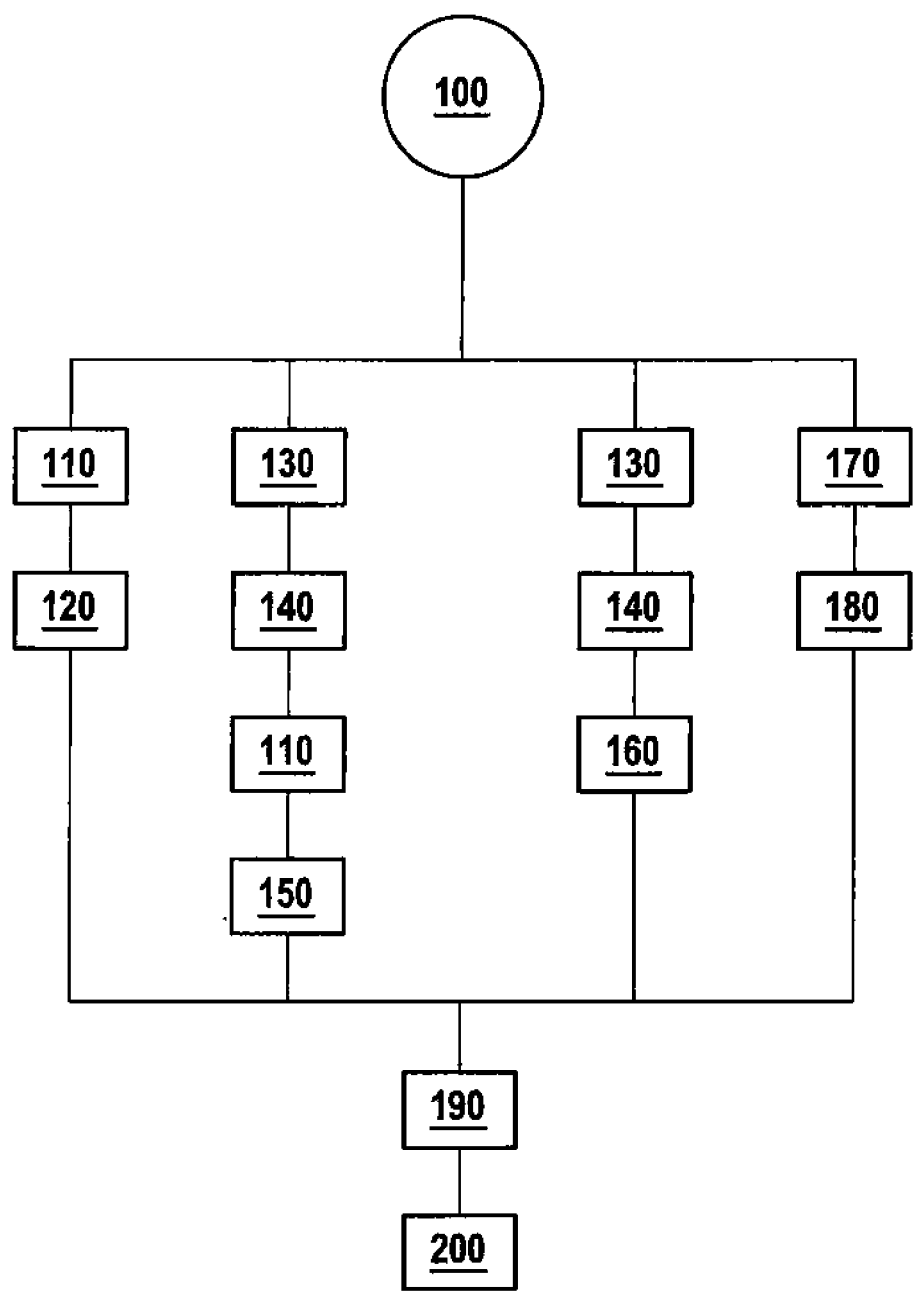
FIG. 3 shows a method for recognizing a wrong driving direction of a motor vehicle in the form of a flow chart.

Wrong-way driving may be detected in step 190 if a respective criterion of one of the four parallel paths from FIG. 3 is met. Otherwise, a verification may be carried out to the extent that the four paths are considered in parallel and each criterion met increases the probability of wrong-way driving. Thus, for example, each path may be assigned a probability of 25 percent. Wrong-way driving then exists, for example, if a certain probability threshold, for example, 75 percent or 100 percent, is exceeded.

In another step 200, a driver of motor vehicle 1 is informed acoustically, haptically and/or visually when wrong-way driving is detected or a wrong driving direction is recognized.

In support of the verification, a wrong driving direction may be recognized if navigation system 12 of motor vehicle 1 detects a position of motor vehicle 1 in the traffic lane 3b or 3c. This is only possible after a stop line has been crossed. This may be implemented in a fifth path not depicted.

The above explanations and figures relate to right hand traffic. The explanations apply analogously to left hand traffic.

What is claimed is:

1. A method for recognizing an entry of a motor vehicle into a traffic lane of a road opposite the driving direction of the traffic lane, comprising:
    detecting a stop line delimiting the traffic lane from an intersection; and
    recognizing a wrong driving direction of the motor vehicle if the motor vehicle has crossed the stop line upon entering the traffic lane.

2. The method as recited in claim 1, wherein a traffic light signal system of the road associated with the traffic lane is detected, and a wrong driving direction is recognized if the stop line is farther away from the motor vehicle than the traffic light signal system.

3. The method as recited in claim 1, wherein a traffic light signal system of the road associated with the traffic lane is detected, and a wrong driving direction is recognized if a rear side of the traffic light signal system is detected.

4. The method as recited in claim 1, wherein a wrong driving direction is recognized if a navigation system of the motor vehicle detects a position of the motor vehicle in the traffic lane.

5. The method as recited in claim 1, wherein the entry of the motor vehicle into a traffic lane is compared with kinematic data of the motor vehicle in order to recognize a wrong driving direction.

6. The method as recited in claim 5, wherein the kinematic data of the motor vehicle is compared with stored kinematic data of a database.

7. The method as recited in claim 5, wherein the motor vehicle transmits the kinematic data of the motor vehicle to a database.

8. The method as recited in claim 2, wherein a driver of the motor vehicle is at least one of acoustically, haptically, and visually informed upon recognition of a wrong driving direction.

9. A detection device for recognizing an entry of a motor vehicle into a traffic lane of a road opposite a driving direction of the traffic lane, comprising:
- a visual sensor unit for detecting a stop line delimiting the traffic lane from an intersection; and
- a control unit including a processor configured to recognize a wrong driving direction of the motor vehicle if the motor vehicle has crossed the stop line upon entry into the traffic lane.

10. The control device and detection device as recited in claim 9, wherein the visual sensor unit is a video camera.

* * * * *